United States Patent
Hamann

(10) Patent No.: US 6,940,064 B2
(45) Date of Patent: Sep. 6, 2005

(54) METHOD AND APPARATUS FOR VALIDATING THE OPERATION OF AN OPTICAL SCANNING DEVICE

(75) Inventor: Oliver Hamann, Sammamish, WA (US)

(73) Assignee: Laser Sensor Technology, Inc., Redmond, WA (US)

( * ) Notice: Subject to any disclaimer, the term of this patent is extended or adjusted under 35 U.S.C. 154(b) by 201 days.

(21) Appl. No.: 10/373,923

(22) Filed: Feb. 24, 2003

(65) Prior Publication Data

US 2003/0160162 A1 Aug. 28, 2003

Related U.S. Application Data

(60) Provisional application No. 60/359,459, filed on Feb. 22, 2002.

(51) Int. Cl.[7] .................................................. H01J 3/14
(52) U.S. Cl. ........................ 250/234; 250/574; 356/338
(58) Field of Search ................................ 250/234–236, 250/574, 216, 221, 222.1, 222.2; 356/335–338, 341, 342, 445

(56) References Cited

U.S. PATENT DOCUMENTS

| | | |
|---|---|---|
| 4,871,251 A | 10/1989 | Preikschat et al. |
| 5,751,423 A | 5/1998 | Traina et al. |
| 6,449,042 B1 * | 9/2002 | Hamann ..................... 356/339 |
| 2002/0140990 A1 * | 10/2002 | Liu ........................... 358/406 |

FOREIGN PATENT DOCUMENTS

| | | |
|---|---|---|
| EP | 0 366 037 A2 | 5/1990 |
| EP | 1 063 512 A2 | 12/2000 |
| WO | WO 02/10717 A2 | 2/2002 |

* cited by examiner

*Primary Examiner*—Kevin Pyo
(74) *Attorney, Agent, or Firm*—Christensen O'Connor Johnson Kindness PLLC

(57) ABSTRACT

An apparatus for validating the operation of an optical scanning system is provided. The apparatus includes one or more scanning illumination beams (6) for scanning an object, and one or more observing beams that comprise light scattered by the object being scanned, which inversely follow the path of the illumination beams. The apparatus further includes a reflector structure (9) arranged to reflect both the illuminating beams and observing beams scattered by a reference target (10) for a portion of each scan (e.g., a scan may be a 360-degree scan in the case of a circular scanning system). The apparatus still further includes the reference target (10) arranged to be scanned by the illumination beams reflected by the reflector structure during said portion of each scan. Light scattered by the reference target is received as the observing beams, and their optical properties are continuously monitored to validate the proper operation of the optical scanning system.

34 Claims, 3 Drawing Sheets

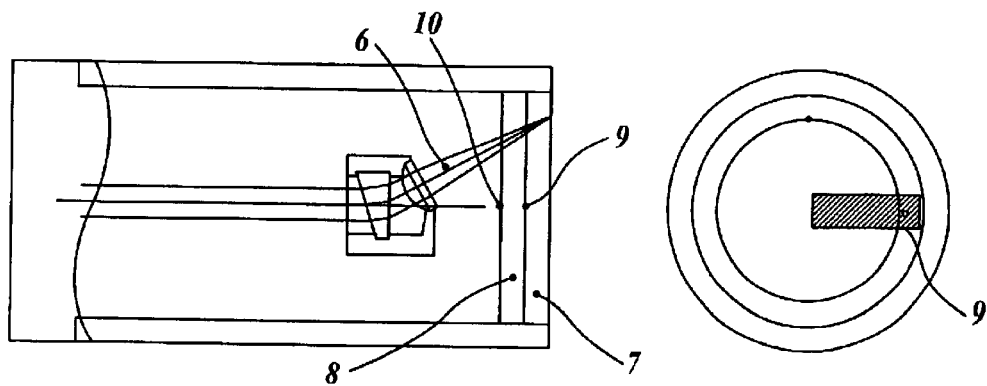
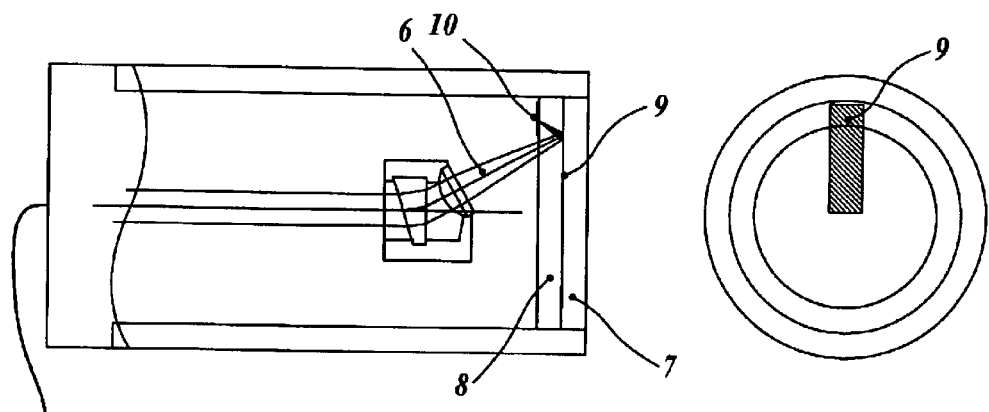
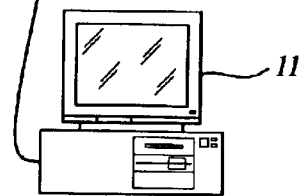
*Fig.3A.*   *Fig.3B.*
*Fig.4A.*   *Fig.4B.*

… …

METHOD AND APPARATUS FOR VALIDATING THE OPERATION OF AN OPTICAL SCANNING DEVICE

CROSS-REFERENCE(S) TO RELATED APPLICATION(S)

The present application claims the benefit under 35 U.S.C. § 119(e) of U.S. Provisional Application Ser. No. 60/359,459, filed Feb. 22, 2002.

FIELD OF THE INVENTION

The present invention is concerned with providing means to validate the operation of a scanning device while the device is in use.

BACKGROUND OF THE INVENTION

For optical instruments used in industrial environments, it is critical to validate the results produced by the instrument without the need to remove the instrument from the process. For instruments using a static intensity signal, for example turbidity meters, this is commonly done by periodically switching the light path by means of a movable mirror or other moving optical devices to observe a "standard" target of known optical properties. If the frequent reading from such a standard remains identical to a first measurement of the standard after calibration, it can be assumed that the measurement results obtained by the instrument are still valid.

This procedure can be carried out while the instrument is inserted into a process environment, yet it requires moving optical elements and a schedule to carry out the standard reference measurements. It would be preferable if no additional moving elements were necessary and the reference measurement could be carried out automatically.

For a scanning optical device, such as the ones based on the Focused Beam Reflectance Measurement (FBRM) as disclosed in U.S. Pat. No. 4,871,251 explicitly incorporated herein by reference but not limited to it, no suitable validation system exists. The present invention describes a method and apparatus for validating a scanning device, including a FBRM-based scanning device.

SUMMARY OF THE INVENTION

In accordance with one aspect of the present invention, an apparatus for validating the operation of an optical scanning system is provided. The apparatus includes one or more scanning illumination beams for scanning an object, and one or more observing beams that comprise light scattered by the object being scanned by the one or more illumination beams. The apparatus further includes a reflector structure arranged to reflect both the one or more illuminating beams and one or more observing beams scattered by a reference target for a portion of each scan (e.g., each scan may be a 360-degree scan in the case of a circular scanning system). The apparatus still further includes the reference target arranged to be scanned by the one or more illumination beams reflected by the reflector structure during said portion of each scan.

In operation, normally, the one or more scanning illumination beams scan an object to be observed, and the light scattered from the object is received as the one or more observing beams, which are then analyzed to obtain information about the scanned object. During a portion of each scan, however, the one or more illumination beams are blocked by the reflector structure and reflected toward the reference target. The reference target receives such reflected beams and scatters light, which forms one or more observing beams. The observing beams scattered by a reference target are then reflected from the reflector structure and analyzed to obtain information about the reference target. The key here is that the optical distance from a light source of the illumination beams to the object to be observed is the same as the optical distance from the same light source to the reference target via the reflector structure. Therefore, by monitoring the optical properties of the light scattered from the reference target per each scan, which should remain constant as long as the optical scanning system is operating properly, it is possible to validate the proper operation of the optical scanning system.

In one embodiment, an optical window is placed in an optical path of the optical scanning system. The window is arranged so as to intersect both the one or more illuminating beams and the one or more observing beams. The window is also arranged so that the object to be observed lies adjacent to the outer surface of the window, wherein the outer surface is defined as a surface opposite the inner surface facing a light source of the one or more illuminating beams. The window may be formed of two individual windows with equal optical thickness adjacent to one another, and these individual windows may sandwich the reflector structure therebetween and further include the reference target on the inner surface of the window.

The present invention further provides a method of validating the operation of an optical scanning system. The method includes generally four steps. The first step involves mounting a reflector structure in an optical path of the optical scanning system such that both an illuminating beam and an observing beam of the optical scanning system are reflected therefrom for a portion of each scan carried out by the scanning system. The second step involves mounting a reference target for receiving the illuminating beam reflected from the reflector structure during the portion of each scan and for scattering such beam into the observing beam, which is then reflected from the reflector structure. The third step involves detecting property values of the observing beam scattered from the reference target and reflected by the reflector structure. Lastly, the fourth step involves comparing the detected property values of the observing beam to predefined nominal property values.

For example, the property values to be detected and compared against the predefined nominal values may be the peak intensity of the detected scattered light from the reference target, the time duration of the detected scattered light from the reference target, or the spectral composition of the detected scattered light from the reference target. Preferably, the nominal property values are pre-established after calibration of the optical scanning system and stored for comparison in a computer system. The computer system can continuously compare the detected property values against the stored nominal values, and analyze and display the results of such comparison. In one embodiment, it is contemplated that the computer system will trigger a validation alarm based on a predefined discrepancy between the detected property values and the nominal values.

The present invention still further provides an apparatus for validating the operation of an optical scanning system, including one or more scanning illumination beams for scanning an object, and one or more observing beams that comprise light scattered by the object being scanned by the one or more illumination beams. The apparatus further includes reflecting means for reflecting both the one or more illuminating beams and one or more observing beams scattered by a reference target for a portion of each scan carried out by the scanning system, and reference means for receiving the one or more illumination beams reflected from the reflecting means during said portion of each scan and for scattering at least a portion of such beams. The apparatus still further includes detection means for receiving the light scattered from the reference means and reflected by the reflecting means, and comparison means for comparing property values of the detected scattered light to predefined nominal property values.

Accordingly, the present invention provides a method and apparatus for validating the proper operation of an optical scanning system, without requiring any moving elements in addition to those already used in the optical scanning system itself. Further, the method and apparatus of the present invention carry out standard reference measurements for the purpose of validation automatically and periodically (per each scan), and thus do not disrupt the normal operation of the optical scanning system.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 3A is a schematic cross-sectional view of an optical scanning device incorporating a validation window of the present invention, illustrating an illumination beam path extending to the outside of the validation window;

FIG. 3B is a schematic end view of the optical scanning device of FIG. 3A;

FIG. 4A is a schematic cross-sectional view of the optical scanning device incorporating a validation window of the present invention (the same as FIG. 3A), illustrating an illumination beam path extending to a reflective structure within the validation window and then to a reference target provided on the inside of the validation window; and FIG. 4B is a schematic end view of the optical scanning device of FIG. 4A, indicating the position of the reflective structure.

DETAILED DESCRIPTION OF THE PREFERRED EMBODIMENT

Figure 1A:
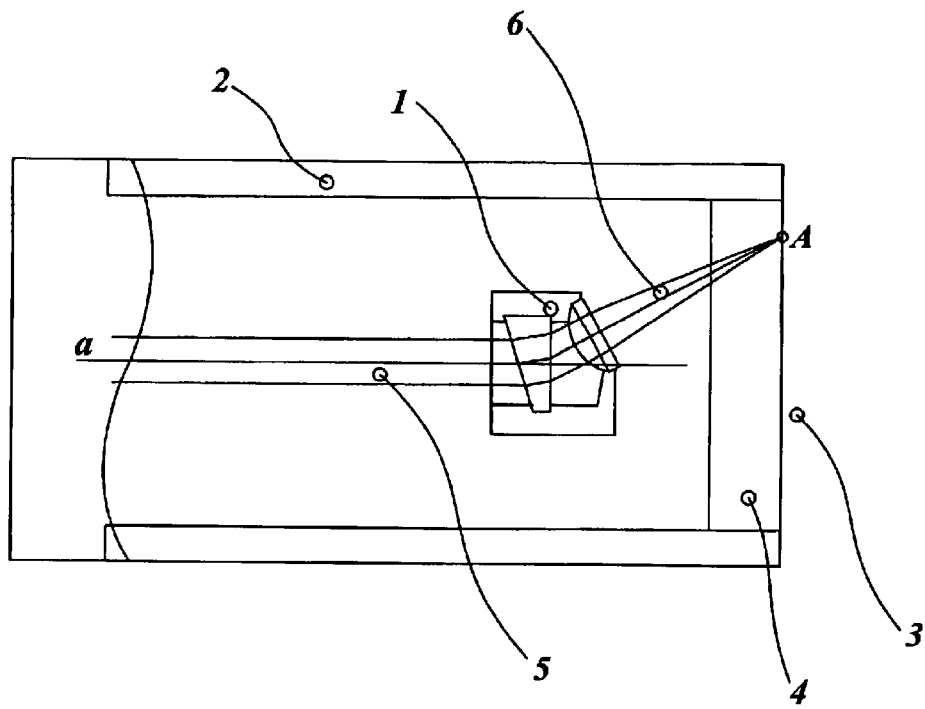
FIG. 1A is a schematic cross-sectional view of an optical scanning device suitable for incorporating a validation system of the present invention.
Figure 1B:
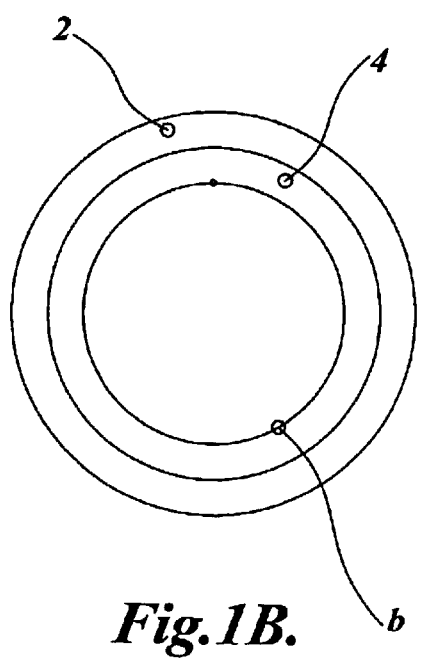
FIG. 1B is a schematic end view of the optical scanning device of FIG. 1A, indicating a circular scan path.

To illustrate the invention, an embodiment suited for use with an FBRM system will be shown. It is obvious, though, that the same principles can be applied to other scanning optical devices. FIG. 1A shows a view of an optical scanner 1 mounted inside a probe tube 2 separated from the surrounding media 3 by means of a window 4. Scanner 1 rotates around mechanical axis a at a known angular velocity. A collimated beam of light 5 from a light source (not shown) enters the scanner 1 and the light is focused through the optical window 4 to a small spot "A" on the outer surface of said window. Referring additionally to FIG. 1B, the rotation of the scanner 1 results in a moving scan spot (such as "A") following a circular path b on the outside of the window 4. If an object, such as a particle in a liquid slurry media 3, is located adjacent to the window 4 and in the scan path b, the focused beam 6 will scan across the object with a known velocity and light will be scattered from the object for the duration of the interaction. A portion of the light falls back into the solid angle that can be observed by the optical scanner 1. The observing light is essentially collimated by said optical scanner 1 and travels on the same path as the illuminating beam 5 in the opposite direction. A beam splitter (not shown) is used later in the optical path to separate illuminating and observing light paths. The time duration of the scattered light pulse is measured and provides information related to the dimension of the observed object, such as a particle. For a more detailed explanation of the operation of an FBRM instrument, refer to U.S. Pat. No. 4,871,251 incorporated by reference above.

Figure 2A:
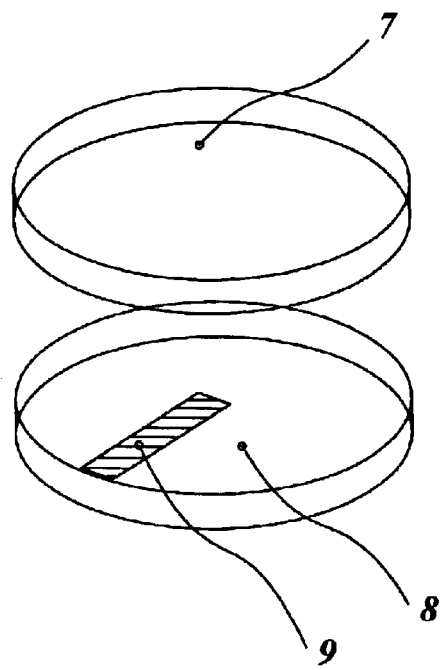
FIG. 2A is an exploded view of one embodiment of a validation window formed in accordance with the present invention.
Figure 2B:
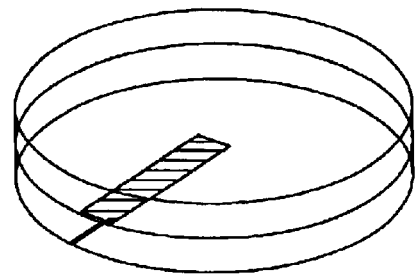
FIG. 2B is an assembled view of the validation window of FIG. 2A.

The present invention provides a method and apparatus for validating or calibrating the reading from a scanning system, by reflecting the light from a light source for a fraction of the time used to complete a full scan onto a reference target located at a distance from the optical scanner 1, which is essentially equal to the distance from the optical scanner 1 to the outer surface of window 4. The key component of the present invention, subsequently to be called a validation window, is a two piece assembly as illustrated in FIGS. 2A and 2B. The validation window consists of an outer window 7 and an inner window 8 of essentially equal optical thickness. The term optical thickness is used here to allow the two windows to be manufactured of different materials, e.g. sapphire for the outer window and BK7 optical glass for the inner window. The physical thickness of each window has to be matched to the refractive index of the respective window material to achieve the same optical performance and hence the equal optical thickness. An index matching liquid may be placed between the inner and outer windows. Of course, the inner and outer windows 7 and 8 may be made of the same material and have the equal physical thickness, as well. A reflective layer 9 structured to obscure part of the scan path is located on the surface of the inner window 8, oriented towards the outer window 7 as shown in FIG. 2A. The shape of the reflective layer 9 shown in FIG. 2A serves an example to illustrate the invention; other shapes and dimensions of the reflective layer or structure are obviously possible. A structured chrome layer is an example of a possible reflective layer, while other materials (metallic, dielectric, hybrid) are possible as well. As a further example, a grating structure may be used as a reflective structure, also.

Figure 2C:
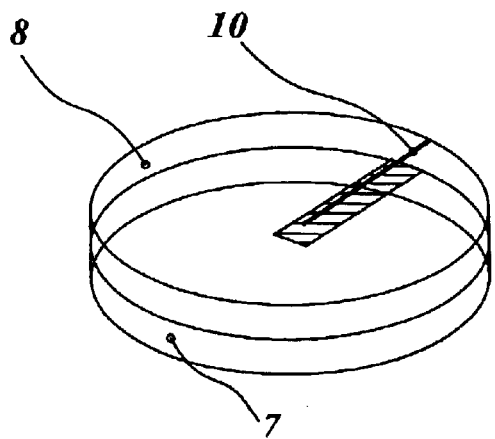
FIG. 2C is a reverse (upside-down) view of the validation window of FIG. 2B, illustrating a reference target in the form of a line applied on the inside surface of the validation window.

When the inner window 8 and outer window 7 are brought into contact, as shown in FIG. 2B, and are incorporated into an optical scanning device as shown in FIG. 1A, the two optical path lengths respectively shown in FIGS. 3A and 4A are essentially equal. Specifically, if the optical scanner 1 is focused to generally have its focal spot on or very near the outside of the outside window 7 (FIG. 3A), a focal spot will be generated on or very near the inside of the inside window 8 as long as the scan beam 6 hits the reflective structure 9 between the two windows. (FIG. 4A.) FIGS. 3B and 4B indicate the respective positions of the reflective structures 9 in these two instances. In other words, for a portion of the complete scan, the focal spot scans across a region on the inside of the validation window instead of the outside. If a reference object, such as a line 10 in FIG. 2C, is placed on the inside surface of the validation window in the region scanned by the beam being reflected by the reflective structure 9, a measurement of the dimension of said reference object 10 is taken with every scan. Specifically, light reflected by the reflective structure 9 to the reference object 10 is scattered from the object 10, and a portion of the scattered light is again reflected by the reflective structure 9 back into the solid angle that can be observed by the optical scanner 1. As a non-limiting example, said reference object 10 could be made by depositing a diffuse scattering material, such as finely pigmented paint, with sharp contours on the inside surface of said validation window.

If all properties of the optical and electronic systems of the optical scanning instrument equipped with said validation window (such as laser power, fiber coupling and bend losses, photo detector response, electronic amplification and signal processing and others directly influencing the measurement of objects) remain constant over time, then the dimension measured with every scan of said reference object 10 will remain constant. If the measurement of the reference object 10 does not change over time, it is safe to assume that the dimensions of other objects measured during the time period when the scanning beam passes through the validation window are measured in a repeatable, calibrated manner. In one embodiment, the dimension measurement of the reference object 10 is carried out by measuring the time duration of the detected light scattered from the reference object 10, though other various optical properties associated with the light scattered from the reference target 10, such as the peak intensity of the detected scattered light, can also be measured, as will be apparent to one skilled in the art. These measurements from the reference object 10 can be compared against nominal values indicative of proper operation of the optical scanning instrument, which preferably are established after calibration of the optical scanning instrument and stored in a computer system 11 (FIG. 4A). In one embodiment, the computer system 11 continuously compares the measured property values of the detected scattered light from the reference object 10 against the prestored nominal values, and analyzes and displays the results of such comparison.

Any change in the measured dimension of the reference object 10 indicates a change in the properties of the optical and electronic systems having a direct influence on the measurement of objects. Therefore, it can be concluded that the instrument does not carry out measurements in a repeatable, calibrated manner. In one embodiment, the computer system 11 is configured to issue a validation alarm if a predefined discrepancy is found between the detected property values and the prestored nominal values.

To be precise, the change in the measured dimension of the reference object 10 does not unambiguously indicate which properties of said optical and electronic systems did change. Nonetheless, for the purpose of instrument validation, the indication that the reference (standard) measurement remains unchanged, as compared to an original calibration, is sufficient to assure that measurements are carried out in a repeatable and calibrated manner.

In one preferred embodiment, electronic means are provided to switch between a "validation mode" and a "measurement mode." In the validation mode, the light source is only operated when the scanning beam is fully blocked by the reflective structure 9. Therefore, for every scan there will be only one measurement taken, originating from the reference object 10. This mode is illustrated in FIGS. 4A and 4B.

In contrast, in the measurement (normal) mode, the light source is only operated when no part of the scanning beam is blocked by the reflective structure 9. Thus, in this mode, only measurements of objects on the outside of the validation window (i.e., in the media 3) are gathered and the results are directly comparable to those acquired with an instrument not equipped with a validation window. This mode is illustrated in FIGS. 3A and 3B. In order to allow for the switching between said modes, a sensing device such as a tachometer indicating the rotational position of the scanner with respect to the reflective structure 9 has to be provided.

While the present disclosure particularly explains the construction and use of the validation system for a scanning optical instrument designed to measure the time duration of back-scattered light pulses, it is obvious to those skilled in the art that a similar approach of placing a reflective structure in a section of the scan path of other scanning optical instruments operating through a window is feasible. For example, if the information gathered by said scanning optical instrument is spectroscopic data, then it is obvious that the reference structure placed on the inside of the validation window will be made of a material with known composition to provide a repeatable reference spectrum. In this example, the property of the detected scattered light to be examined would be the spectral composition of the scattered light.

While the preferred embodiments of the invention have been illustrated and described, it will be appreciated that various changes can be made therein without departing from the spirit and scope of the invention.

What is claimed is:

1. An apparatus for validating the operation of an optical scanning system, comprising:
   one or more scanning illumination beams for scanning an object;
   one or more observing beams that comprise light scattered by the object being scanned by the one or more illumination beams;
   a reflector structure arranged to reflect both the one or more illuminating beams and one or more observing beams scattered by a reference target for a portion of each scan carried out by said scanning system; and
   the reference target arranged to be scanned by the one or more illumination beams reflected by the reflector structure during said portion of each scan;
   wherein light scattered by said reference target is measurable in a repeatable manner.

2. An apparatus according to claim 1, wherein an optical window is placed in an optical path of the optical scanning system, said window intersecting both the one or more illuminating beams and the one or more observing beams.

3. An apparatus according to claim 2, wherein said window is placed in the optical path of the optical scanning system such that the object to be scanned lies adjacent to the outer surface of the window, the outer surface being defined as a surface opposite the inner surface of the window that is facing a source of the one or more illuminating beams.

4. An apparatus according to claim 3, wherein said window comprises two individual windows with equal optical thickness adjacent to one another, said individual windows having said reflector structure arranged between them and said reference target arranged on the inner surface of the window.

5. An apparatus according to claim 4, wherein said reference target is line shaped and arranged essentially perpendicular to the scan direction of the optical scanning system.

6. An apparatus according to claim 4, wherein said two individual windows are made from the same material and have equal physical thickness.

7. An apparatus according to claim 4, wherein an index matching liquid is located between said two individual windows.

8. An apparatus according to claim 1, wherein the dimensions of said reference target is predetermined.

9. An apparatus according to claim 1, wherein said reference target is made of a material with known spectroscopic properties.

10. An apparatus according to claim 1, wherein said reflector structure is a metallic structure.

11. An apparatus according to claim 1, wherein said reflector structure is a dielectric structure.

12. An apparatus according to claim 1, wherein said reflector structure is a grating structure.

13. An apparatus according to claim 1, further comprising means for switching between a validation mode and a measurement mode, wherein, during the validation mode a light source of the one or more illuminating beams is operated only during said portion of each scan, while during the measurement mode the light source is operated except for said portion of each scan.

14. A method of validating the operation of an optical scanning system, comprising the steps of:

mounting a reflector structure in an optical path of the optical scanning system such that both an illuminating beam and an observing beam of said optical scanning system are reflected therefrom for a portion of each scan carried out by said scanning system;

mounting a reference target for receiving the illuminating beam reflected from the reflector structure during the portion of each scan and scattering the same into the observing beam toward the reflector structure;

detecting property values of the observing beam scattered from the reference target and reflected by the reflector structure; and comparing the detected property values to predefined nominal property values.

15. A method according to claim 14, wherein an optical window is placed in the optical path of the optical scanning system, said window intersecting both the illuminating beam and the observing beam.

16. A method according to claim 15, wherein said window is placed in the optical path of the optical scanning system such that an object to be scanned lies adjacent to the outer surface of the window, the outer surface being defined as a surface opposite the inner surface of the window that is facing a source of the illuminating beam.

17. A method according to claim 16, wherein said window comprises two individual windows with equal optical thickness adjacent to one another, said individual windows having said reflector structure arranged between them and said reference target arranged on the inner surface of the window facing the source of the illuminating beam.

18. A method according to claim 17, wherein said reference target is line shaped and arranged essentially perpendicular to the scan direction of the optical scanning system.

19. A method according to claim 17, wherein said two individual windows are made from the same material and have equal physical thickness.

20. A method according to claim 17, wherein an index matching liquid is located between said two individual windows.

21. A method according to claim 14, wherein the dimensions of said reference target is predetermined.

22. A method according to claim 14, wherein said reference target is made of a material with known spectroscopic properties.

23. A method according to claim 14, wherein said reflector structure is a metallic structure.

24. A method according to claim 14, wherein said reflector structure is a dielectric structure.

25. A method according to claim 14, wherein said reflector structure is a grating structure.

26. A method according to claim 14, wherein said property values of the observing beam comprise the peak intensity of the detected scattered light.

27. A method according to claim 14, wherein said property values of the observing beam comprise the time duration of the detected scattered light.

28. A method according to claim 14, wherein said property values of the observing beam comprise the spectral composition of the detected scattered light.

29. A method according to claim 14, wherein the step of comparing the detected property values to predefined nominal property values comprises using a computer data acquisition system.

30. A method according to claim 29, wherein said nominal property values are established after calibration of the optical scanning system and stored for comparison in the computer data acquisition system.

31. A method according to claim 29, wherein said detected property values are continuously compared to said nominal property values and the results of said comparison are displayed and analyzed.

32. A method according to claim 31, wherein a predefined discrepancy between said detected property values and said nominal property values triggers a validation alarm.

33. An apparatus for validating the operation of an optical scanning system, comprising:

one or more scanning illumination beams for scanning an object;

one or more observing beams that comprise light scattered by the object being scanned by the one or more illumination beams;

reflecting means for reflecting both the one or more illuminating beams and one or more observing beams scattered by a reference target for a portion of each scan carried out by said scanning system;

reference means for receiving the one or more illumination beams reflected from said reflecting means during said portion of each scan and for scattering at least a portion of the one or more illumination beams;

detection means for receiving the light scattered from the reference means and reflected by the reflecting means; and comparison means for comparing property values of the detected scattered and reflected light to predefined nominal property values.

34. An apparatus according to claim 33, wherein the comparison means comprises a computer.

* * * * *